United States Patent [19]

Breuer et al.

[11] Patent Number: 5,338,731

[45] Date of Patent: * Aug. 16, 1994

[54] BISPHOSPHONATES, PROCESSES FOR PREPARATION AND PHARMACEUTICAL COMPOSITIONS CONTAINING THE SAME

[75] Inventors: Eli Breuer, Jerusalem; Gershon Golomb, Efrat, both of Israel

[73] Assignee: Yissum, Research Development Company of the Hebrew University of Jerusalem, Jerusalem, Israel

[ * ] Notice: The portion of the term of this patent subsequent to Mar. 23, 2010 has been disclaimed.

[21] Appl. No.: 28,905

[22] Filed: Mar. 8, 1993

Related U.S. Application Data

[60] Continuation-in-part of Ser. No. 764,035, Sep. 23, 1991, Pat. No. 5,196,409, which is a division of Ser. No. 570,266, Aug. 20, 1990, abandoned.

[30] Foreign Application Priority Data

Aug. 20, 1989 [IL]   Israel ......................... 91362

[51] Int. Cl.$^5$ .................. A61K 31/66; C07F 9/40; C07F 9/38
[52] U.S. Cl. ................... 514/108; 558/158; 558/161; 562/20
[58] Field of Search ............... 558/158, 161; 562/20; 514/108

[56] References Cited

U.S. PATENT DOCUMENTS 3,012,054 12/1961  Moss ...................... 558/160
4,060,546 11/1977  Blaser et al. .............. 562/22

FOREIGN PATENT DOCUMENTS 1010965 12/1957  Fed. Rep. of Germany .
1072346 12/1959  Fed. Rep. of Germany .

OTHER PUBLICATIONS

Kanaan et al, Phosphorous and Sulfur, 1988, vol. 37, pp. 217–229.
Hilderbrand, CRC, "The Role of Phosphonates in Living Systems", pp. 55–96 1980.
Hilderbrand, CRC, "The Role of Phosphonates in Living Systems", pp. 161–188 1980.
Rafik Karaman et al, Acylphosphonic Acids and Methyl Hydrogen Acylphosphonates: Physical and Chemical Properties and Theoretical Calculations, J. Chem. Soc. 1989.
Chem. Abstr. 1988, 110(2), 13646e.
Chem. Abstr. 1988, 109(7), 54960a; BE 1000075A1, Feb. 02, 1988.
The Merck Index; Eleventh Edition; Merck: Rahway, NJ, 1989; No. 1512.
Gallez, B. et al, Appl. Radiat. Isot. 1988, 39(9), 1011–14.

Primary Examiner—Robert W. Ramsuer
Assistant Examiner—Michael G. Ambrose
Attorney, Agent, or Firm—Lowe, Price, LeBlanc & Becker

[57] ABSTRACT

Bisphosphonate compounds are of the Formula (I):

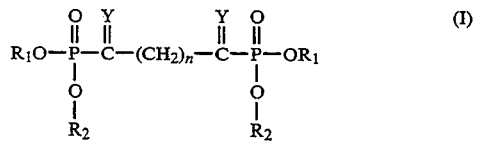

wherein Y is =O or =N—OH and n is from 3 to 24, and further wherein when Y is =O, (i) $R_1$ is hydrogen and $R_2$ is sodium, or (ii) $R_1$ is sodium and $R_2$ is methyl, and when Y is =N—OH, $R_1$ is sodium and $R_2$ is methyl.

39 Claims, 3 Drawing Sheets

BISPHOSPHONATES, PROCESSES FOR PREPARATION AND PHARMACEUTICAL COMPOSITIONS CONTAINING THE SAME

RELATED APPLICATIONS

This application is a continuation-in-part of U.S. application Ser. No. 07/764,035 filed Sep. 23, 1991, U.S. Pat. No. 5,196,409 which is a divisional application of U.S. application Ser. No. 07/570,266 filed Aug. 20, 1990 abandoned.

FIELD OF THE INVENTION

The present invention relates to novel bisphosphonates, processes for their preparation and pharmaceutical compositions containing the same. The compounds and the pharmaceutical compositions according to the present invention are suitable and useful for the treatment of irregularities in calcium metabolism.

BACKGROUND OF THE INVENTION

There are several pathological conditions which involve irregularities in calcium metabolism. Such conditions comprise bone related diseases including Paget's disease and osteoporosis, as well as osteolysis in bone metastases.

Bone metastases present a major problem in many frequently occurring malignancies. Hypercalcemia, resulting from bone resorption, is a common and very important complication of malignancy, causing distressful symptoms, such as severe pain and spontaneous fractures, and may lead to a metabolic coma and death. Moreover, neoplastic cell-induced osteolysis may determine the localization and growth enhancement of the tumor. (G. R. Mundy, Bone, 8, supp. 1, S9-5 16 (1987); Calcium in Biological Systems, R. P. Rubin, G. B. Weiss, and J. W. Putney, Jr. eds. Plenum Press, N.Y. (1985)). Ectopic calcification is a seemingly opposite type of pathological condition, characterized by the deposition of calcium phosphate in a number of clinically important diseases including, for example, atherosclerosis, kidney and renal calculus, arthritis, and bioprosthetic heart valve calcification, and implanted biomaterial calcification such as bioprosthetic and prosthetic heart valves, vascular grafts, LVAD (left ventricular assist devices), contact lenses and entire artificial hearts.

In some common bone disorders, the balance between the process of resorption and formation remains normal, but the rate of bone turnover is much higher. Most cases of primary hyperparathyroidism, Paget's disease and thyroxicosis are in this category. In other common diseases such as osteoporosis, there is an imbalance between resorption and formation. Whether increased resorption or impaired formation predominates, however, the consequence is the same, i.e. diminished total bone mass. This lowering in the bone mass continues until it falls below the critical fracture threshold (B. D. Boyan, "New Therapies for Age-related Bone Disease", *Hospital Practice*, 26; supp. 1, 1991).

Bisphosphonates are a relatively new class of drugs that have been developed for use in various metabolic diseases of bone, the target being excessive bone resorption and inappropriate calcification and ossification. (M. D. Francis and R. R. Martodam, in "The Role of Phosphonates in Living Systems" R. L. Hilderbrand, ed., CRC Press, Boca Raton, Fla., 1983, pp. 55-96; H. Fleisch, Bone, 1987, 8, Supp. 1, S23-S28). Recently there have been reports of encouraging clinical trials utilizing bisphosphonates to treat osteoporosis and hypercalcemia in patients with breast cancer, myeloma, and bronchial carcinoma related osteolytic metastases, in addition to the established usage of bisphosphonates in Paget's disease and for diagnostic purposes in bone mapping. However, bisphosphonate therapy is frequently accompanied by severe side effects. Bisphosphonates have been also found highly potent both in inhibiting bioprosthetic heart valve calcification, and in experimental arteriosclerosis. However, this was accompanied by severe adverse effects on bone development and overall somatic growth.

Currently used bisphosphonates belong to the geminal type, in which the two phosphoryl groups are bound to the same carbon ("P—C—P"), and therefore may be viewed as pyrophosphate analogs in which the oxygen between the two phosphorus atoms is replaced by a carbon.

In contrast, monophosphonates, vicinal bisphosphonates (P—C—C—P) and compounds in which the distance between the phosphoryl groups is longer (P—(C-)$_n$—P, n>2) are reported to be less active or inactive at all.

U.S. Pat. No. 3,012,054 dated Mar. 18, 1960 and M. Kanaan and R. Burgada, Phosphorus and Sulfur, 1988, 37, 217-229, describe the preparation of "tetraalkyl esters of diphosphonates" having the structure:

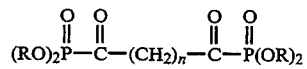

wherein R is an alkyl radical containing 1-4 carbons and n is 2 to 8, inclusive. The cited patent deals only with tetraesters. It is well known that such dialkyl acylphosphonates, as mentioned, exhibit extreme instability toward water, and they hydrolyze to the corresponding carboxylic acids both in acidic and alkaline conditions. Consequently, hydrolysis of the tetraalkyl esters described in the patent and the paper cited above would lead to dicarboxylic acids HOOC—(CH$_2$)$_n$—COOH. Therefore, the syntheses of dealkylated derivatives such as represented by the formulas below:

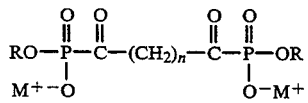

and

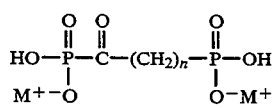

require special nonhydrolytic methods, and by no means are the dealkylated compounds obvious derivatives of the tetraesters.

Neither esters nor acids of bisphosphonates in which the two ketophosphonic groups are aromatic rings or the like have been reported.

From the results obtained in various clinical studies using conventional bisphosphonates, it appears that there is a need for compounds which have greater margin between the bone resorption inhibiting effect and that inhibiting mineralization, without an increase in toxicity.

SUMMARY OF THE INVENTION

According to the present invention it was found that introduction of modifications into long chain bisphosphonates of the type P—(C)$_n$—P increases the cation binding ability of these compounds, and inhibits ectopic calcification. The advantage of this type of compound in interacting with calcium phosphate crystals is assumed to derive from the presence of at least one additional independent anchor site in the molecule as compared with known bisphosphonates. Additional advantages of this novel class of compounds are an effect of long duration and the enhanced ability to interact with the cell membrane.

The present invention relates to novel bisphosphonates of the formula (I)

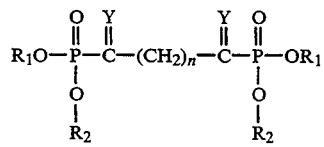

wherein Y is =O or =N—OH and n is from 3 to 24, and further wherein when Y is =O, (i) $R_1$ is hydrogen and $R_2$ is sodium, or (ii) $R_1$ is sodium and $R_2$ is methyl, and when Y is =N—OH, $R_1$ is sodium and $R_2$ is methyl.

The present invention further relates to processes for obtaining the above-mentioned compounds according to formula (I), pharmaceutical compositions containing the same, and methods for treating irregularities in calcium metabolism or the symptoms associated therewith.

DETAILED DESCRIPTION

Figures 1, 1A:
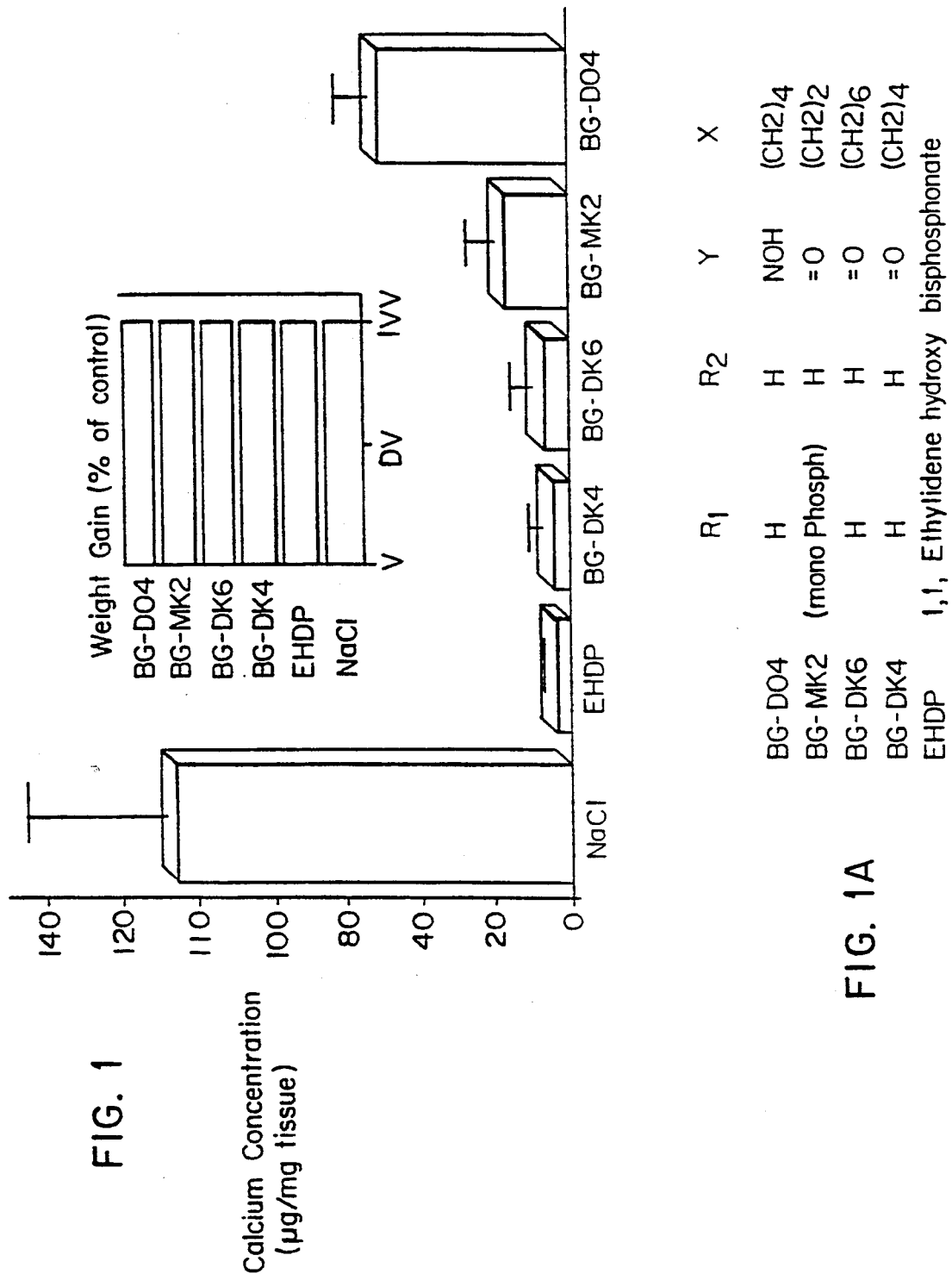
FIG. 1 sets forth results of in-vivo testing of bisphosphonate compounds for preventing calcium precipitation.

The bisphosphonate compounds of the present invention are of the formula (I):

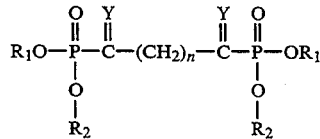

wherein Y is =O or =N—OH and n is from 3 to 24, and further wherein when Y is =O, (i) $R_1$ is hydrogen and $R_2$ is sodium, or (ii) $R_1$ is sodium and $R_2$ is methyl, and when Y is =N—OH, $R_1$ is sodium and $R_2$ is methyl.

Thus, more specific embodiments of the bisphosphonate compounds of the present invention are of the following formulae (II)-(IV):

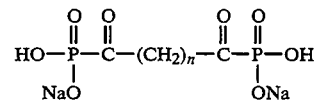

wherein n is from 4 to 24,

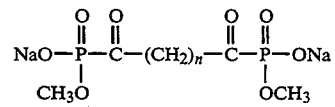

wherein n is from 4 to 24, and

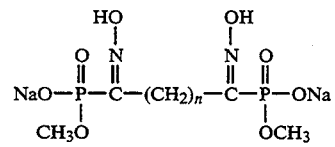

wherein n is from 3 to 24.

The process for preparing dihydrogen disodium α,α'-diketobisphosphonate disalts of formula (II) generally comprises adding bromotrimethylsilane to the corresponding tetramethyl diketobisphosphonate, followed by addition of sodium hydroxide to the reaction product.

The process for the preparation of tetraalkyl α,α'-diketobisphosphonates, particularly when n, representing the number of alkylene units, is from 3 to 11, comprises adding trimethyl phosphite to the corresponding dicarboxylic acid dihalide. The process for preparing bisacylphosphonates derived from higher dicarboxylic acids generally comprises adding oxalyl chloride to the corresponding dicarboxylic acid and, after completion of the reaction and removal of excess oxalyl chloride, adding trimethyl phosphite to the resulting product.

The process for preparing dimethyl α,α'-diketobisphosphonate disodium salts of formula (III) comprises adding the corresponding tetramethyl diketobisphosphonate to sodium iodide.

The process for preparing dimethyl α,α'-bis(hydroxyiminophosphonate) disalts of formula (IV) comprises combining a sodium ethoxide solution with hydroxylamine hydrochloride and adding the resulting product to the corresponding dimethyl disodium α,α-bisacylphosphonate.

These processes are demonstrated in detail in the examples.

The present invention also relates to pharmaceutical compositions which comprise a compound according to the invention as an active ingredient and suitable carriers, optionally suitable for controlled release delivery systems, and/or other additives.

The drug delivery systems may include any conventional suitable carrier or controlled release system (sustained release, delayed action preparations), based on a polymeric vehicle (e.g. silicone, polyurethane, or any other biocompatible polymer), or based on degradable systems (e.g. chitosan, collagen, or any other degradable/biodegradable carrier), including bioresorbable systems.

Chitosan is soluble only in acidic pH, preferably by acetic acid. Drug delivery systems based on chitosan as a carrier can be prepared in a conventional manner or in an innovative manner. In the first method the drug is dissolved with the polymer under acidic pH conditions (preferably, 1 to 10% w/w solids with acetic acid), and the solvent is evaporated or extracted by a non-solvent. By this method sustained release drug delivery systems in the form of film (matrix), micromatrics, microcapsules or microspheres could be prepared.

An innovative method of preparing a chitosan-based drug delivery system is based on the alkalinity of chitosan (amino functional groups) and the acidity of phosphonates (as free acid obtained from the sodium salt by a cationic exchange resin). The drug in its acid form is reacted with chitosan yielding a soluble chitosan-phosphonate salt with the requirement for only limited amount of another exterior acid, followed by water evaporation/extraction as above. By this method the controlled release of the drug is governed not only by the matrix but also by the dissociation of the carrier-drug salt. An additional advantage is the possible targeting of the drug by chitosan. The chitosan-phosphonate salt could be embedded in chitosan for further delay of drug release.

The treatment with the controlled release delivery system is utilized by subdermal implantation (as was done in the studies illustrated in FIG. 1) or by site specific implantation, with the aim being optimization of therapy, using lower dosage, minimizing systemic side effects, and effective prolonged treatment with better patient compliance.

The novel bisphosphonates, according to the present invention, prevent calcium precipitation from metastable calcium and phosphate solution. Profound inhibition of rat, subdermal biprosthetic heart valve tissue calcification was achieved, by coimplantation of Alzet osmotic pumps releasing the drug, and tissue cusps. Therapy was achieved without side effects, as exhibited by the normal somatic growth. These in-vivo results are summarized in FIGS. 1-1A.

The novel bisphosphonates, according to the present invention are useful in the treatment of the following diseases: osteoporosis (including disuse and postmenopausal osteoporosis), hypercalcemia of malignancy, (direct) anticancer effect, heterotopic ossification (hip arthroplasty, spinal cord injury, myositis ossificans), Paget's disease and hyperphosphatemia (e.g. diabetes).

It can be seen that these compounds are useful not only for direct treatment of various diseases but also for treatment of the symptoms of the diseases (e.g. hyperphosphatemia or hypercalcemia).

The compounds according to the present invention are also useful as diagnostics in, for example, nuclear medicine.

The compounds according to the present invention may also possess industrial applications which are listed below (R. L. Hilderbrand, The Role of Phosphonates in Living Systems, Chapter 7, page 172, CRC Press): adhesives; agents for extraction, concentration, and purification of uranium, thorium, and plutonium; antioxidants; antistatic agents; blowing agents; catalysts; corrosion inhibitors; coupling agents; crystallization inhibitors; dentifrice compositions; deodorants; detergent additives; detergents for cleaning metal surfaces; dye modifiers; flame retardants for polymers; flame retardants for textiles; fire retardants for synthetic fibers; flotation agents; fuel additives; gelling agents; hardening oil composites; heat and light stabilizers; hydraulic fluid additives; ion exchange resins; lubricants; photography; plasticizers; polyester, polyethylene, and polycarbonate discoloration inhibitors; polyurethane additives; rayon additives; resin and plastic additives; scale inhibitors; settling retardants; sequestering agents; solvent extraction; suspending agents; synthetic fiber preparation; viscosity modifiers; wood fireproofing agents and the like.

The invention is further illustrated by means of the following non-limiting examples.

EXAMPLE 1

This example demonstrates a typical procedure for preparing bisacylphosphonates derived from lower dicarboxylic acids, for example, wherein n, the number of methylene units, is from 3 to 11. Generally, the method for the synthesis of tetraalkyl $\alpha,\alpha'$-diketobisphosphonates comprises adding trimethyl phosphite (0.4 mole) dropwise to the dicarboxylic acid dichloride (0.2 mole) at 5° C. After the addition is completed, the reaction mixture is allowed to stir for 1 hour at ambient temperature. The procedure was employed to prepare tetramethyl adipoylbisphosphonate (n=4) in a yield of 90%. IR (neat) 1697s, 1260s, 1030s cm$^{-1}$. NMR; (CDCl$_3$) $^1$H: $\delta$ 3.87 (12H, J=10.64 Hz), 2.85 (4H, m), 1.65 (4H, m). $^{31}$p: $-0.57$ ppm (sept., J=11 Hz).

EXAMPLES 2–8

The procedure of Example 1 was repeated using various dicarboxylic acid dichlorides to prepare the following compounds:

EXAMPLE 2

Tetramethyl suberoylbisphosphonate (n=6) was obtained in a yield of 90%. IR spectrum (neat) 1697s, 1265s, 1034s cm$^{-1}$. NMR (CDCl$_3$); $^1$H: $\delta$ 3.87 (12H, d, J=10.85 Hz), 2.82 (4H, t, J=7.2 Hz), 1.63 (4H, m), 1.32 (4H, m), $^{31}$P: $\delta$=0.88 (sept) $^{31}$P: $-0.44$ (sept).

EXAMPLE 3

Tetramethyl pimeloylbisphosphonate (n=5) $^{31}$P: $-0.56$ (sept, J=10 Hz).

EXAMPLE 4

Tetramethyl azelaoylbisphosphonate (n=7) $^{31}$P: $-0.50$ (sept, J=10.5 Hz).

EXAMPLE 5

Tetramethyl sebacoylbisphosphonate (n=8) $-$P: $-0.48$ (sept, J=10.4 Hz).

EXAMPLE 6

Tetramethyl 1,12-dioxododecane-1,12-bisphosphonate (n=10)

NMR (toluene) $^{31}$P: $-0.55$ (sept, J=10.9 Hz).

EXAMPLE 7

Tetramethyl 1,13-dioxotridecane-1,13-bisphosphonate (n=11)

$^{31}$P: 0.78 (sept, J=10.2 Hz).

EXAMPLE 8

Tetramethyl 1,14-dioxotetradecane-1,14-bisphosphonate (n=12)

$^{31}$P: 0.87 (sept, J=10 Hz).

The compounds of these examples were sufficiently pure to be used for the next steps in syntheses of latter compounds without further purification. However, the compounds decomposed upon attempted distillation.

EXAMPLE 9

This example demonstrates a typical procedure for preparing bisacylphosphonates derived from higher dicarboxylic acids, for example, for preparing compounds wherein n is from 12 to 24. In preparing tetramethyl 1,16-dioxohexadecane-1,16-bisphosphonate (n=14), to hexadecanedioic acid (10.0 g, 0.035 mol) was added oxalyl chloride (15 ml, 0.17 mol). The reaction mixture was stirred at 60°-65° C. for 2 h. After the excess oxalyl chloride was removed by evaporation under reduced pressure, the residue was dissolved in dry toluene (50 ml) and trimethyl phosphite (9.92 g, 0.08 mol) was added to the solution at 0° C. under nitrogen with stirring. The solution was stirred overnight at room temperature, cooled and the product precipitated. The solid product was recrystallized from dry to toluene. M.p. 55°-58° C., yield, 10.4 g, 64%. P-31 NMR: $\delta = -1$ ppm, septet.

EXAMPLES 10-17

The procedure of Example 9 was repeated using various dicarboxylic acids to prepare the following compounds:

EXAMPLE 10

Tetramethyl 1,15-dioxopentadecane-1,15-bisphosphonate (n=13)
$^{31}P$: −0.68 (sept, J=10.3 Hz).

EXAMPLE 11

Tetramethyl 1,17-dioxoheptadecane-1,17-bisphosphonate (n=15)
$^{31}P$: −0.63 (sept, J=10.8 Hz).

EXAMPLE 12

Tetramethyl 1,18-dioxooctadecane-1,18-bisphosphonate (n=16)
$^{31}P$: −0.88 (sept, J=10.4 Hz).

EXAMPLE 13

Tetramethyl 1,19-dioxononadecane-1,19-bisphosphonate (n=17)
$^{31}P$: −0.72 (sept, J=10.5 Hz).

EXAMPLE 14

Tetramethyl 1,20-dioxoeicosane-1,20-bisphosphonate (formula (II), n=18)
$^{31}P$: −0.85 (sept, J=10.9 Hz).

EXAMPLE 15

Tetramethyl 1,22-dioxodocosane-1,22-bisphosphonate (n=20)
$^{31}P$: −0.78 (sept, J=9.4 Hz).

EXAMPLE 16

Tetramethyl 1,24-dioxotetracosane-1,24-bisphosphonate (n=22)
$^{31}P$: −0.76 (sept, J=9.8 Hz).

EXAMPLE 17

Tetramethyl 1,26-dioxohexacosane-1,26-bisphosphonate (n=24)
$^{31}P$: −0.87 (sept, J=10.3 Hz).

The compounds of these examples were sufficiently pure to be used for the next steps in the syntheses of latter compounds without further purification. However, the compounds decomposed upon attempted distillation.

EXAMPLE 18

This example demonstrates a general method for the synthesis of dihydrogen disodium $\alpha,\alpha'$-diketobisphosphonate disalts of Formula (II). 0.01 mole of a tetramethyl diketobisphosphonate of Formula (II) was dissolved in dry acetonitrile (20 ml). 0.066 mole (9 ml) of bromotrimethylsilane was added slowly and the reaction mixture was stirred at the ambient temperature for three hours. The acetonitrile was evaporated in vacuum while maintaining the temperature below 30°. A solution of sodium hydroxide (0.02 mole) in methanol (25 ml) was added to the residue and the reaction mixture is stirred overnight at the ambient temperature. The white precipitate was filtered, washed with methanol (15 ml) and dried. This method was employed to prepare dihydrogen disodium 1,16-dioxohexadecane-1,16-bisphosphonate, Formula (II), n=14, as follows: To tetramethyl 1,16-dioxohexadecane-1,16-bisphosphonate (10.4 g, 0.022 mol) dissolved in dry toluene was added dropwise at 0° C. bromotrimethylsilane (27.3 g, 0.178 mol). The solution was stirred at 40°-50° C. for 2.5 h and evaporated to dryness. The residue was dissolved in absolute methanol (150 ml) and a solution of sodium hydroxide (1.77 g, 0.044 mol) in methanol (100 ml) was added slowly. The precipitated product was collected by filtration and washed by 2×50 ml methanol. M.p. >250° C., yield 10 g 97%. NMR $^1H$: 2.80 ppm 4H, 1.62 ppm 4H 1.25 ppm 20 H, $^{31}P$: −2.22 ppm Anal. Calcd. for $C_{16}H_{30}Na_2O_8P_2$: M.W. 458. C, 41.92; H, 6.55; P, 13.53. Found: C, 42.08; H, 6.42; P, 13.86.

EXAMPLES 19-35

The procedure of Example 18 was repeated using various tetramethyl bis (acylphosphonates) to prepare the following compounds:

EXAMPLE 20

Dihydrogen disodium 1,7-dioxoheptane-1,7-bisphosphonate (Formula (II), n=5) Anal. Calcd. for $C_7H_{12}Na_2O_8P_2$: M.W. 332 C, 25.30; H, 3.61; P, 18.67. Found: C, 25.50; H, 3.47; P, 18.39.

EXAMPLE 21

Dihydrogen disodium 1,8-dioxooctane-1,8-bisphosphonate (Disodium dihydrogen suberoylbisphosphonate) (Formula (II), n=6) yield 90%, m.p.>250° C., IR (KBr) 1677s, 1214s, 1110s, 1075s cm$^{-1}$. NMR ($D_2O$) $^1H$: $\delta$ 2.8 (4H, t, J=7.2 Hz), 1.58 (4H, m), 1.31 (4H, m), $^{31}P$: $\delta$=−3.23, 3.7 s. Anal. Calcd. C, 27.75; H, 4.05, Found, C, 26.93; H, 3.92. Anal. Calcd. for $C_8H_{14}Na_2O_8P_2$: C, 27,74; H, 4.04; P, 17.91. Found: C, 27.53; H, 4.35; P, 17.56.

EXAMPLE 22

Dihydrogen disodium 1,9-dioxononane-1,9-bisphosphonate (Formula (II), n=7) Anal. Calcd. for $C_9H_{16}Na_2O_8P_2$: M.W. 360. C, 30.00; H, 4.44; P, 17.22. Found: C, 29.71; H, 4.20; P, 17.47.

EXAMPLE 23

Dihydrogen disodium 1,10-dioxodecane- 1,10-bisphosphonate (Formula (II), n=8) NMR $^1H$: 2.80 4H, 1.59 4H, 1.32 8H; $^{31}P$ −0.71 ppm. Anal. Calcd. for $C_{10}H_{18}Na_2O_8P_2$: M.W. 374. C, 32.08; H, 4.81; P, 16.57. Found: C, 31.92; H, 5.02; P, 16.40.

EXAMPLE 24

Dihydrogen disodium 1,11-dioxoundecane-1,11-bisphosphonate (Formula (II), n=9 ) Anal. Calcd. for $C_{11}H_{20}Na_2O_8P_2$: M.W. 388. C, 34.02; H, 5.15; P, 15.97. Found: C, 34.00; H, 5.13; P, 16.09.

EXAMPLE 25

Dihydrogen disodium 1,12-dioxododecane-1,12-bisphosphonate (Formula (II), n=10)Anal. Calcd. for $C_{12}H_{22}Na_2O_8P_2$: M.W. 402. C, 35.82; H, 5.47; P, 15.42. Found: C, 36.05; H, 5.52; P, 15.29.

EXAMPLE 26

Dihydrogen disodium 1,13-dioxotridecane-1,13-bisphosphonate (Formula (II), n=11) Anal. Calcd. for $C_{13}H_{24}Na_2O_8P_2$: M.W. 416. C, 37.50; H, 5.76; P, 14.90. Found: C, 37.25; H, 5.52; P, 15.19.

EXAMPLE 27

Dihydrogen disodium 1,14-dioxotetradecane-1,14-bisphosphonate (Formula (II), n=12) Anal. Calcd. for $C_{14}H_{26}Na_2O_8P_2$: M.W. 430. C, 39.06; H, 6.04; P, 14.41. Found: C, 38.95; H, 5.96; P, 14.12.

EXAMPLE 28

Dihydrogen disodium 1,15-dioxopentadecane-1,15-bisphosphonate (Formula (II), n=13 ) Anal. Calcd. for $C_{15}H_{28}Na_2O_8P_2$: M.W. 444. C, 40.54; H, 6.30; P, 13.96. Found: C, 40.73; H, 5.98; P, 14.07.

EXAMPLE 29

Dihydrogen disodium 1,17-dioxoheptadecane-1,17-bisphosphonate (Formula (II), n=15) Anal. Calcd. for $C_{17}H_{32}Na_2O_8P_2$: M.W. 472. C, 43.22; H, 6.77; P, 13.11. Found: C, 43.12; H, 6.46; P, 13.34.

EXAMPLE 30

Dihydrogen disodium 1,18-dioxooctadecane-1,18-bisphosphonate (Formula (II), n=16) Anal. Calcd. for $C_{18}H_{34}Na_2O_8P_2$: M.W. 486. C, 44.44; H, 6.99; P, 12.75. Found: C, 44.16; H, 6.77; P, 12.64.

EXAMPLE 31

Dihydrogen disodium 1,19-dioxononadecane-1,19-bisphosphonate (Formula (II), n=17) Anal. Calcd. for $C_{19}H_{36}Na_2O_8P_2$: M.W. 500. C, 45.60; H, 7.20; P, 12.40. Found: C, 45.63; H, 7.32; P, 12.17.

EXAMPLE 32

Dihydrogen disodium 1,20-dioxoeicosane-1,20-bisphosphonate (Formula (II), n=18) Anal. Calcd. for $C_{20}H_{38}Na_2O_8P_2$: M.W. 514. C, 46.69; H, 7.39; P, 12.06. Found: C, 46.53; H, 7.23; P, 12.10.

EXAMPLE 33

Dihydrogen disodium 1,22-dioxodocosane-1,22-bisphosphonate (Formula (II), n=20) NMR $^1H$, 2.85 4H, 1.65 4H, 1.29 32H; $^{31}P$ −2.32 ppm. Anal. Calcd. for $C_{22}H_{42}Na_2O_8P_2$: M.W. 542. C, 48.70; H, 7.74; P, 11.43. Found: C, 48.57; H, 7.49; P, 11.53.

EXAMPLE 34

Dihydrogen disodium 1,24-dioxotetracosane-1,24-bisphosphonate (Formula (II), n=22) Anal. Calcd. for $C_{24}H_{46}Na_2O_8P_2$: M.W. 570. C, 50.52; H, 8.07; P, 10.87. Found: C, 50.54; H, 8.27; P, 10.74.

EXAMPLE 35

Dihydrogen disodium 1,26-dioxohexacosane-1,26-bisphosphonate (Formula (II), n=24) Anal. Calcd. for $C_{26}H_{50}Na_2O_8P_2$: M.W. 598. C, 52.17; H, 8.36; P, 10.36. Found: C, 51.98; H, 8.37; P, 10.74.

EXAMPLE 36

This example demonstrates the general method for the synthesis of dimethyl α,α'-diketobisphosphonate disodium salts (Formula III). A tetramethyl diketobisphosphonate (0.5 mole) was dissolved in 50 ml dry acetone or acetonitrile, and the solution was added to a solution of sodium iodide (1.1 mole) in dry acetone (130 ml). The reaction mixture was stirred overnight at room temperature. The precipitate was filtered, washed with dry acetone or acetonitrile and dried. The yields are greater than 85%. This method was employed to prepare dimethyl disodium adipoylbisphosphonate (Formula (III) n=4), yield 95%, m.p.>250°,IR (nujol): 1660s, 1210s, 1110s, 1020s cm$^{-1}$. NMR (D$_2$O) $^1H$: δ 3.6 (6H, d, J=10.67 Hz), 2.85 (4H, m), 1.6 (4H, m).

EXAMPLES 37–52

The procedure of Example 36 was repeated using various tetramethyl diketobisphosphonates to prepare the following compounds:

EXAMPLE 37

Dimethyl disodium suberoylbisphosphonate (Formula (III), n=6), yield 100%, m.p.>250° C. IR nujol 1670s, 1216s, 1110s, 1040s cm$^{-1}$. NMR (D$_2$O) $^1H$ δ 3.65 (6H, d, J=10.56 Hz), 2.87 (4H, t, J=7.2 Hz), 1.64 (4H, m) 1.36 (4H, m) $^{31}P$: 0.30 (q, J=11.4 Hz).

EXAMPLE 38

Dimethyl disodium pimeloylbisphosphonate (Formula (III), n=5) $^{31}P$: 0.42 (q, J=11.0 Hz).

EXAMPLE 39

Dimethyl disodium azelaoylbisphosphonate (Formula (III), n=7) $^{31}P$: 0.38 (q, J=10.8 Hz).

EXAMPLE 40

Dimethyl disodium sebacoylbisphosphonate (Formula (III), n=8) $^{31}P$: 0.50 (q, J=11.0 Hz).

EXAMPLE 41

Dimethyl disodium 1,12-dioxododecane-1,12-bisphosphonate (Formula (III), n=10) $^{31}P$: 0.47 (q, J=10.4 Hz).

EXAMPLE 42

Dimethyl disodium 1,13-dioxotridecane-1,13-bisphosphonate (Formula (III), n=11) $^{31}P$: 0.25 (q, J=10.0 Hz).

EXAMPLE 43

Dimethyl disodium 1,14-dioxotetradecane-1,14-bisphosphonate (Formula (III), n=12) $^{31}P$: 0.32 (q, J=10.7 Hz).

EXAMPLE 44

Dimethyl disodium 1,15-dioxopentadecane-1,15-bisphosphonate (Formula (III), n=13) $^{31}P$: 0.62 (q, J=10 Hz).

EXAMPLE 45

Dimethyl disodium 1,16-dioxohexadecane-1,16-bisphosphonate (Formula (III), n=14) $^{31}P$: 0.44 (q, J=9.4 Hz).

EXAMPLE 46

Dimethyl disodium 1,17-dioxoheptadecane- 1,17-bisphosphonate (Formula (III), n=15) $^{31}P$: 0.40 (q, J=10.1Hz).

EXAMPLE 47

Dimethyl disodium 1,18-dioxooctadecane-1,18-bisphosphonate (Formula (III), n=16) $^{31}P$: 0.35 (q, J=10.5 Hz).

EXAMPLE 48

Dimethyl disodium 1,19-dioxonodadecane-1,19-bisphosphonate (Formula (III), n=17) $^{31}P$: 0.29 (q, J=10.7 Hz).

EXAMPLE 49

Dimethyl disodium 1,20-dioxoeicosane-1,20-bisphosphonate (Formula (III), n=18) $^{31}P$: 0.37 (q, J=11.3 Hz).

EXAMPLE 50

Dimethyl disodium 1,22-dioxodocosane-1,22-bisphosphonate (Formula (III), n=20) $^{31}P$: 0.80 (q, J=10.4 Hz).

EXAMPLE 51

Dimethyl disodium 1,24-dioxotetracosane-1,24-bisphosphonate (Formula (III), n=22) $^{31}P$: 0.72 (q, J=10.1 Hz).

EXAMPLE 52

Dimethyl disodium 1,26-dioxohexacosane-1,26-bisphosphonate (Formula (III), n=24) $^{31}P$: 0.64 (q, J=10.1 Hz).

EXAMPLE 53

This example demonstrates a general procedure for the synthesis of dimethyl α,α'-bis(hydroxyiminophosphonate) disalts of Formula (IV). 0.01 mole of dimethyl disodium α,α'-bisacylphosphonate of Formula (III) was suspended in absolute ethanol (10 ml), in flask A. In a separate flask B, 0.03 mol sodium was dissolved in absolute ethanol (10 ml), in an ice bath under a reflux condenser, equipped with a calcium chloride tube. The resulting solution was added slowly to a solution of 0.03 mol hydroxylamine hydrochloride in methanol (15 ml), until the solution was neutral to pH paper. After stirring for 5 minutes in an ice bath, sodium chloride was filtered and washed with ethanol and the filtrate was added to the solution of dimethyl disodium salt in flask A. The reaction mixture was left to stir for 1–2 days at the ambient temperature, after which it was filtered, washed successively with acetonitrile and ether and dried in vacuo at room temperature. This method was employed to prepare dimethyl disodium 1,6-bishydroxyiminohexane-1,6-bisphosphonate (Formula (IV), n=4) in a yield of 90%, m.p.>250°, IR (KBr): 1650w,b, 1221s, 1085s, 1049s cm$^{-1}$. NMR (D$_2$O) $^1$H: δ 3.55 (6H, d, J=10.8 Hz), 2.5 (4H, m), 1.62 (4H, m). Anal. Calcd. for C$_8$H$_{16}$N$_2$Na$_2$O$_8$P$_2$, M.W. 376: C, 25.53; H, 4.25; N, 7.44; P, 16.48. Found: C, 25.41; H, 3.93; N, 7.62; P, 16.37.

EXAMPLES 54–70

The procedure of Example 53 was repeated using various dimethyl disodium α,α'-bisacylphosphonates to prepare the following compounds:

EXAMPLE 54

Dimethyl disodium 1,7-bishydroxyiminoheptane-1,7-bisphosphonate (Formula (IV), n=5) Anal. Calcd. for C$_9$H$_{18}$N$_2$Na$_2$O$_8$P$_2$: M.W. 390 C, 27.69; H, 4.61; N, 7.17; P 15.89. Found: C, 27,71; H, 4.43; N, 7.23; P, 15.57.

EXAMPLE 55

Dimethyl disodium 1,8-bishydroxyiminooctane- 1,8-bisphosphonate (Formula (IV), n=6) yield 90%, m.p.>250°, IR (KBr); 1665w,b, 1227s, 1087s, 1050s cm$^{-1}$. NMR (D$_2$O): $^1$H δ 3.56 (6H, d, J=10.89 Hz), 2.5 (4H, m), 1.6 (4H, m), 1.4 (4H, m), $^{31}$P 9.32 q. Anal. Calcd. for C$_{10}$H$_{20}$N$_2$Na$_2$O$_8$P$_2$: M.W. 404. C, 29.70; H, 4.95; N, 6.93; P, 15.34. Found: C, 30.02; H, 5.11; N, 6.78; P, 15.42.

EXAMPLE 56

Dimethyl disodium 1,9-bishydroxyiminononane-1,9-bisphosphonate (Formula (IV), n=7) Anal. Calcd. for C$_{11}$H$_{22}$N$_2$Na$_2$O$_8$P$_2$: M.W. 418. C, 31.57; H, 5.26; N, 6.69; P, 14.83. Found: C, 31,50; H, 5.18; N, 6.62; P, 15.01.

EXAMPLE 57

Dimethyl disodium 1,10-bishydroxyiminodecane-1,10-bisphosphonate (Formula (IV), n=8) Anal. Calcd. for C$_{12}$H$_{24}$N$_2$Na$_2$O$_8$P$_2$: M.W. 432. C, 33.33; H, 5.55; N, 6.48; P, 14.35. Found: C, 33.15; H, 5.42; N, 6.39; P, 14.37.

EXAMPLE 58

Dimethyl disodium 1,11-bishydroxyiminoundecane-1,11-bisphosphonate (Formula (IV), n=9) Anal. Calcd. for C$_{13}$H$_{26}$N$_2$Na$_2$O$_8$P$_2$: M.W. 446. C, 34.97; H, 5.82; N, 6.27; P, 3.90. Found: C, 34.75; H, 5.71; N, 6.33; P, 13.79.

EXAMPLE 59

Dimethyl disodium 1,12-bishydroxyiminododecane-1,12-bisphosphonate (Formula (IV), n=10) Anal. Calcd. for C$_{14}$H$_{28}$N$_2$Na$_2$O$_8$P$_2$: M.W. 460. C, 36.52; H, 6.08; N, 6.08; P, 13.47. Found: C, 36.76; H, 5.98; N, 5.90; P, 13.62.

EXAMPLE 60

Dimethyl disodium 1,13-bishydroxyiminotridecane-1,13-bisphosphonate (Formula (IV), n=11) Anal. Calcd. for C$_{15}$H$_{30}$N$_2$Na$_2$O$_8$P$_2$: M.W. 474. C, 37.97; H, 6.32; N, 5.90; P, 13.08. Found: C, 38.03; H, 6.48; N, 6.10; P, 13.05.

EXAMPLE 61

Dimethyl disodium 1,14-bishydroxyiminotetradecane-1,14-bisphosphonate (Formula (IV), n=12) Anal. Calcd. for C$_{16}$H$_{32}$N$_2$Na$_2$O$_8$P$_2$: M.W. 488. C, 39.34; H, 6.55; N, 5.73; P, 12.70. Found: C, 39.53; H, 6.44; N, 5.55; P, 12.80.

EXAMPLE 62

Dimethyl disodium 1,15-bishydroxyiminopentadecane-1,15-bisphosphonate (Formula (IV), n=13 ) Anal. Calcd. for C$_{17}$H$_{34}$N$_2$Na$_2$O$_8$P$_2$: M.W. 502. C, 40.63; H, 6.77; N, 5.57; P, 12.35. Found: C, 40.72; H, 6.56; N, 5.43; P, 12.24.

EXAMPLE 63

Dimethyl disodium 1,16-bishydroxyiminohexadecane-1,16-bisphosphonate (Formula (IV), n=14) NMR $^1$H 3.52 ppm 6H d, 2.42, 4H, 1.54 4H, 1.28 2OH, $^{31}$P 8.78 ppm. Anal. Calcd. for $C_{18}H_{36}N_2Na_2O_8P_2$: M.W. 516. C, 41.86; H, 6.97; N, 5.42; P, 12.01. Found: C, 41.76; H, 6.79; N, 5.35; P, 12.04.

EXAMPLE 64

Dimethyl disodium 1,17-bishydroxyiminoheptadecane-1,17-bisphosphonate (Formula (IV), n=15) Anal. Calcd. for $C_{19}H_{38}N_2Na_2O_8P_2$: M.W. 530. C, 43.01; H, 7.16; N, 5.28; P, 11.69. Found: C, 43.13; H, 7.23; N, 5.40; P, 11.87.

EXAMPLE 65

Dimethyl disodium 1,18-bishydroxyiminooctadecane-1,18-bisphosphonate (Formula (IV), n=16) Anal. Calcd. for $C_{20}H_{40}N_2Na_2O_8P_2$: M. W. 544. C, 44.11; H, 7.35; N, 5.14; P, 11.39. Found: C, 44.32; H, 7.53; N, 5.40; P, 11.17.

EXAMPLE 66

Dimethyl disodium 1,19-bishydroxyiminononadecane-1,19-bisphosphonate (Formula (IV), n=17) Anal. Calcd. for $C_{21}H_{42}N_2Na_2O_8P_2$: M.W. 558. C, 45.16; H, 7.52; N, 5.01; P, 11.11. Found: C, 45.35; H, 7.37; N, 4.87; P, 11.17.

EXAMPLE 67

Dimethyl disodium 1,20-bishydroxyiminoeicosane-1,20-bisphosphonate (Formula (IV), n=18) Anal. Calcd. for $C_{22}H_{44}N_2Na_2O_8P_2$: M.W. 572. C, 46.15; H, 7.69; N, 4.89; P, 10.83. Found: C, 46.37; H, 7.76; N, 4.70; P, 11.03.

EXAMPLE 68

Dimethyl disodium 1,22-bishydroxyiminodocosane-1,22-bisphosphonate (Formula (IV), n=20) NMR $^1$H 3.55 ppm 6H d, 2.50, 4H, 1.59 4H, 1.30 32H, $^{31}$P 8.50 ppm. Anal. Calcd. for $C_{24}H_{48}N_2Na_2O_8P_2$: M.W. 600. C, 48.00; H, 8.00; N, 4.66; P, 10.33. Found: C, 48.06; H, 7.89; N, 4.77; P, 10.44.

EXAMPLE 69

Dimethyl disodium 1,24-bishydroxyiminotetracosane-1,24-bisphosphonate (Formula (IV), n=22) Anal. Calcd. for $C_{26}H_{52}N_2Na_2O_8P_2$: M.W. 628. C, 49.68; H, 8.28; N, 4.45; P, 9.87. Found: C, 49.62; H, 8.33; N, 4.40; P, 9.71.

EXAMPLE 70

Dimethyl disodium 1,26-bishydroxyiminohexacosane-1,26-bisphosphonate (Formula (IV), n=24) Anal. Calcd. for $C_{28}H_{56}N_2Na_2O_8P_2$: M.W. 656. C, 51.21; H, 8.53; N, 4.26; P, 9.45. Found: C, 51.30; H, 8.51; N, 4.40; P, 9.63.

EXAMPLE 71

In this example, dimethyl disodium 1,5-bishydroxyiminopentane-1,5-bisphosphonate (Formula (IV), n=3) was synthesized by the following procedure. Tetramethyl glutarylbisphosphonate dioxime (tetramethyl 1,5-bishydroxyiminopentane-1,5-bisphosphonate) was first prepared as follows: Glutaryl chloride (8.0 g, 0.0473 mole) was added dropwise with stirring to a solution of trimethyl phosphite (20.5 g, 0.165 mol) in toluene (50 ml) at −10° C. under a nitrogen atmosphere over a period of about one hour. During this time the reaction vessel was subjected three times to vacuum of approximately 30 mm for 3–4 minutes to remove the methyl chloride formed in the reaction. At the end of evacuation the pressure was restored by introducing dry nitrogen into the flask. After the completion of the addition, the reaction mixture was stirred at 25° C. for 35 min. Monitoring the reaction by P-31 NMR spectroscopy revealed peaks at 23.5, 22, 18.5, 18, 17.5, 11.5, 7.5, comprising about 60% of the total integrated areas, and a peak belonging to the desired product at −1 ppm (septet). The toluene and excess trimethyl phosphite were evaporated in vacuo to yield an oily product in purity of 40–60% P-31 NMR: 0.5 ppm (sept. J=10 Hz). This product was immediately dissolved in toluene (60 ml), and to the solution was added hydroxylamine hydrochloride (8.2 g, 0.118 mol) followed by dry pyridine (9.34 g, 0.118 mol). After stirring the reaction mixture at ambient temperature for 24 h, the solvent was evaporated (t=40° C. in 1-2 mm vacuum), water (20 ml) was added to the residue followed by dilute hydrochloric acid (20%) to provide an acidic pH, and the obtained mixture was extracted with dichloromethane (2×20 ml). The product, which crystallized slowly from the aqueous solution, maintained at room temperature for 1–2 weeks, was recrystallized from a minimal quantity of water and dried in a vacuum desiccator (1–2 ram, 7 h) over $P_2O_5$. Yield 6 g. 1H NMR (D$_2$O): d 3.72 (6H, d, j=10.5 Hz), 2.50 (4H, m), 1.83 (2H,m); $^{31}$P 14.30 (sept., J=10.5 Hz).

In the second step, to tetramethyl glutarylbisphosphonate dioxime (2.5 g, 0.008 mol) dissolved in acetone (400 ml) was added a solution of sodium iodide (4.77 g, 0.032 mol) in acetone (30 ml). The solution was stirred at 40° C. until P-31 NMR examination showed the completion of the reaction. The precipitate was allowed to settle, the solvent was decanted, a fresh portion of acetone (100 ml) was added to the precipitate and stirring was continued for an additional hour. The product was isolated by filtration, washed with acetone and dried in vacuum (1–2 mm, room temperature). Yield 2.1 g (90%), IR (KBr): 1665w, 1450m, 1200s, 1090s, 1050s; $^1$NMR (D$_2$O): d 3.55 (3H, d, J=11.0 Hz), 2.51 (4H, m), 1.82 (2H, m); $^{31}$P 8.20. Anal. Calcd for $C_7H_{14}N_2Na_2O_8P_2$: M.W. 362. C, 23.20; H, 3.86; N, 7.73; P, 17.12. Found: C, 23.01; H, 4.12; N, 7.80; P, 17.54.

IN VITRO TEST

A novel bisphosphonate according to the present invention was added to a mixture of calcium chloride and sodium phosphate. After a period of time the calcium and phosphorus concentration in the filtrate was determined.

Figure 2:
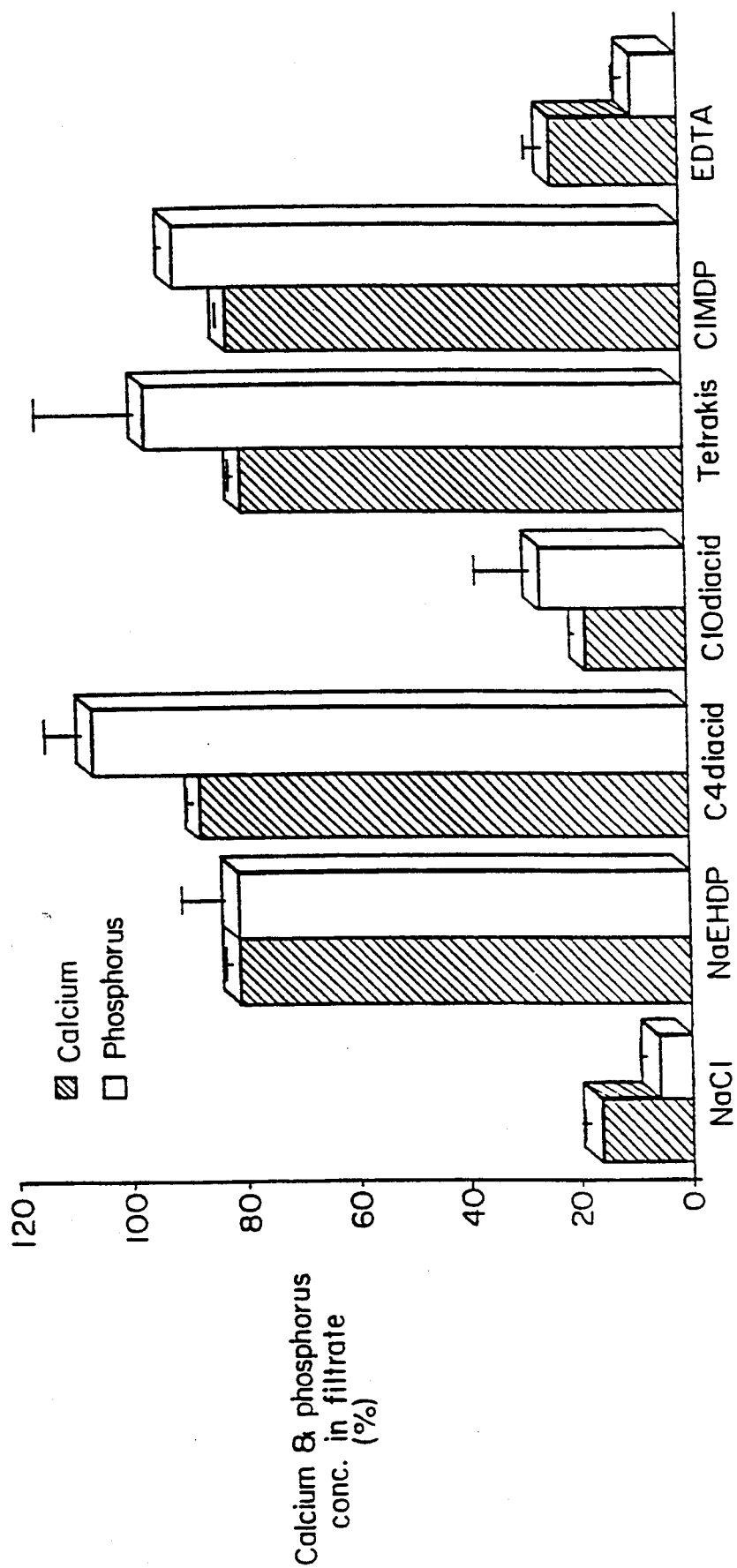
FIG. 2 sets forth the results of calcium and phosphorous precipitation using bisphosphonate compounds.

FIG. 2 shows that adipoylbisphosphonate (C4 diacid)

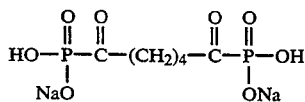

prevents the precipitation of calcium and phosphorus in the solution highly effectively while the C10 analog is less effective. The tetrakisphosphonate is also highly effective. The above novel phosphonates were compared to two commercial compounds

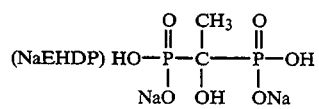

and to

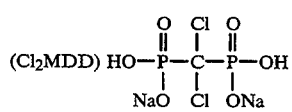

IN VIVO TEST

Figure 3:
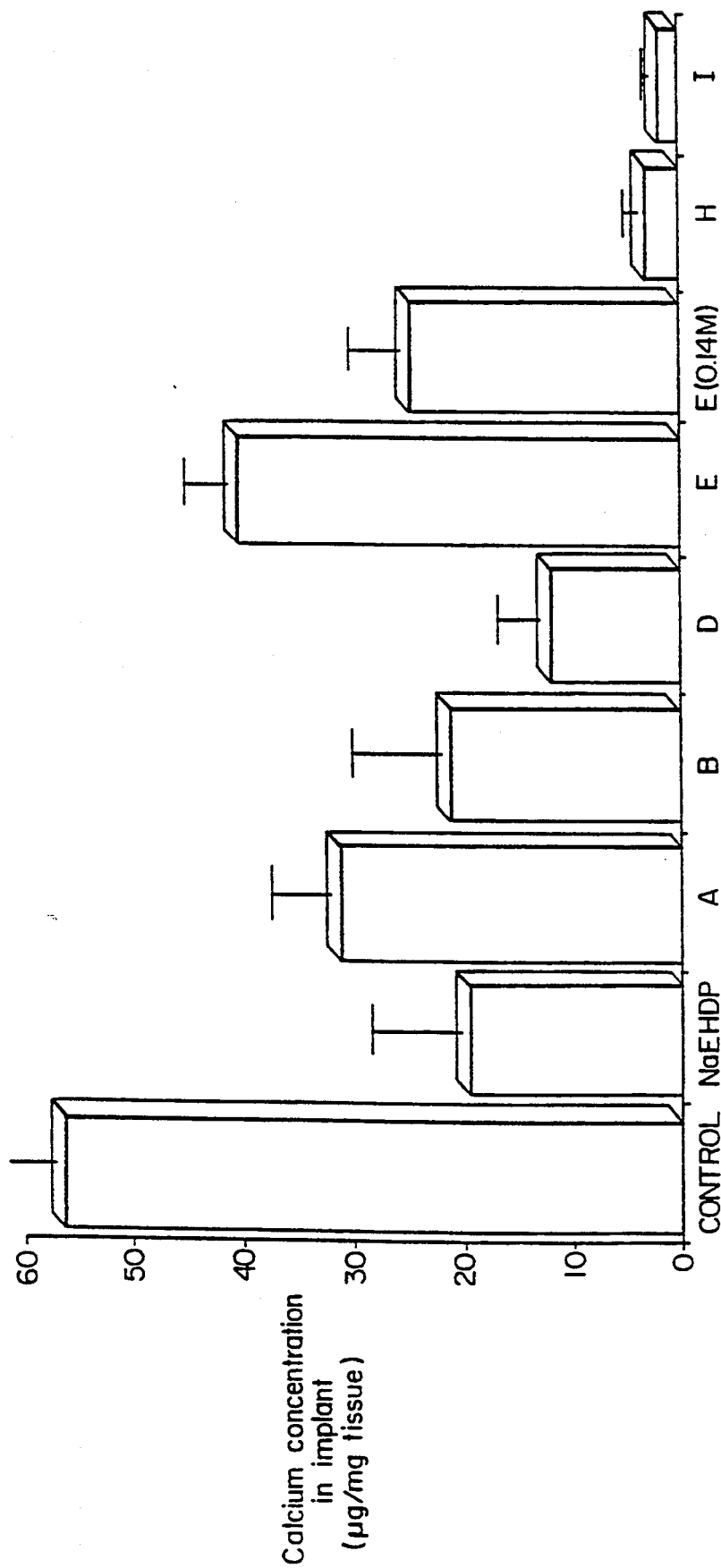
FIG. 3 sets forth in-vivo anti-calcification effects of bisphosphonate compounds.

FIG. 3 shows in vivo anticalcification effect of novel bisphosphonates.

The novel bisphosphonates were:

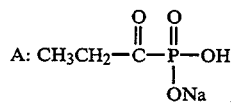

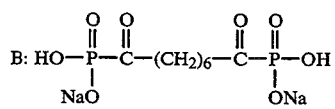

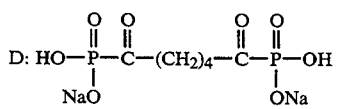

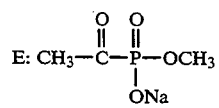

They were compared to the commercial compounds:

H: Cl₂MDP

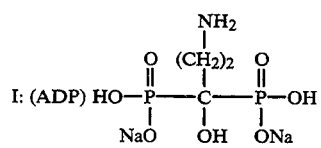

and to NaEHDP.

Additionally, significant inhibition of bone resorption was exhibited in rats by the compound of Formula (II), n=4 (G. Golomb et al., Pharm. Res., Vol. 9, p. 1018 (1992)).

The preceding examples, in vitro tests and in vivo tests are set forth to illustrate specific embodiments of the invention and are not intended to limit the scope of the compounds, compositions or methods of the present invention. Additional embodiments and advantages within the scope of the claimed invention will be apparent to one of ordinary skill in the art.

We claim:

1. Bisphosphonate compounds of the Formula (II):

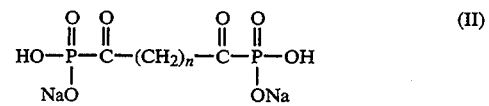

wherein n is 5, 7-9, 11-18, 20, 22 or 24.

2. Bisphosphonate compounds of the Formula (III):

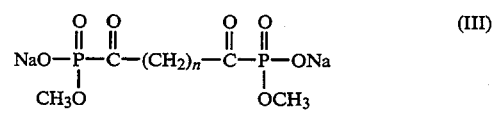

wherein n is from 4 to 24.

3. Bisphosphonate compounds of the Formula (IV):

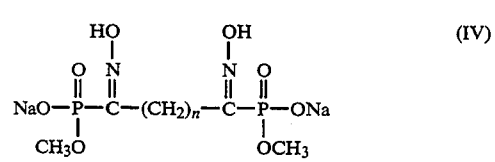

wherein n is 4-18, 20, 22 or 24.

4. A compound according to claim 1, having the formula

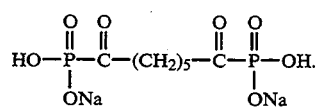

5. A compound according to claim 1, having the formula

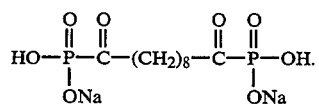

6. A compound according to claim 1, having the formula

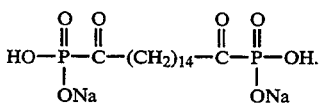

7. A compound according to claim 1, having the formula

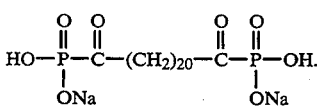

8. A compound according to claim 3, having the formula

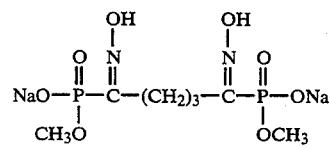

9. A compound according to claim 3, having the formula

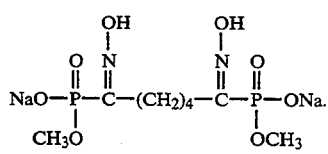

10. A compound according to claim 3, having the formula

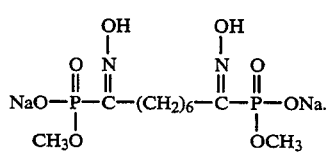

11. A compound according to claim 3, having the formula

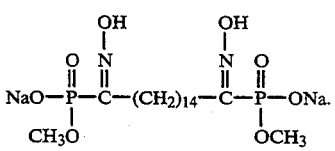

12. A compound according to claim 3, having the formula

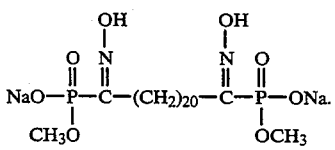

13. A pharmaceutical composition comprising an effective amount of a compound according to claim 1 and a pharmaceutically acceptable excipient or carrier.

14. Pharmaceutical composition according to claim 13, wherein the carrier is suitable for a controlled release delivery system.

15. Pharmaceutical composition according to claim 14, wherein the carrier is based on a polymeric vehicle.

16. Pharmaceutical composition according to claim 15, wherein said polymeric vehicle is based on silicone, polyurethane, or other biocompatible polymer.

17. Pharmaceutical composition according to claim 14, wherein the carrier is based on a degradable bioresorbable system.

18. Pharmaceutical composition according to claim 17, wherein said degradable carrier is based on chitosan, collagen or other biodegradable carrier.

19. Pharmaceutical composition according to claim 14, wherein the controlled release delivery system is adapted for subdermal implantation.

20. Pharmaceutical composition according to claim 14 wherein the controlled release delivery system is adapted for site specific implantation.

21. A method for treating calcium related disorders or the symptoms associated therewith comprising administering to a host an effective amount of a compound according to claim 1.

22. A pharmaceutical composition comprising an effective amount of a compound according to claim 2 and a pharmaceutically acceptable excipient or carrier.

23. Pharmaceutical composition according to claim 22, wherein the carrier is suitable for a controlled release delivery system.

24. Pharmaceutical composition according to claim 23, wherein the carrier is based on a polymeric vehicle.

25. Pharmaceutical composition according to claim 24, wherein said polymeric vehicle is based on silicone, polyurethane, or other biocompatible polymer.

26. Pharmaceutical composition according to claim 23, wherein the carrier is based on a degradable bioresorbable system.

27. Pharmaceutical composition according to claim 26, wherein said degradable carrier is based on chitosan, collagen or other biodegradable carrier.

28. Pharmaceutical composition according to claim 23, wherein the controlled release delivery system is adapted for subdermal implantation.

29. Pharmaceutical composition according to claim 23 wherein the controlled release delivery system is adapted for site specific implantation.

30. A method for treating calcium related disorders or the symptoms associated therewith comprising administering to a host an effective amount of a compound according to claim 2.

31. A pharmaceutical composition comprising an effective amount of a compound according to claim 4 and a pharmaceutically acceptable excipient or carrier.

32. Pharmaceutical composition according to claim 31, wherein the carrier is suitable for a controlled release delivery system.

33. Pharmaceutical composition according to claim 32, wherein the carrier is based on a polymeric vehicle.

34. Pharmaceutical composition according to claim 33, wherein said polymeric vehicle is based on silicone, polyurethane, or other biocompatible polymer.

35. Pharmaceutical composition according to claim 32, wherein the carrier is based on a degradable bioresorbable system.

36. Pharmaceutical composition according to claim 35, wherein said degradable carrier is based on chitosan, collagen or other biodegradable carrier.

37. Pharmaceutical composition according to claim 32, wherein the controlled release delivery system is adapted for subdermal implantation.

38. Pharmaceutical composition according to claim 32 wherein the controlled release delivery system is adapted for site specific implantation.

39. A method for treating calcium related disorders or the symptoms associated therewith comprising administering to a host an effective amount of a compound according to claim 3.

* * * * *